United States Patent [19]

Golden

[11] Patent Number: 4,962,761
[45] Date of Patent: * Oct. 16, 1990

[54] THERMAL BANDAGE

[76] Inventor: Theodore A. Golden, 762 Wooddale Rd., Birmingham, Mich. 48010

[*] Notice: The portion of the term of this patent subsequent to Jul. 11, 2006 has been disclaimed.

[21] Appl. No.: 347,093

[22] Filed: May 4, 1989

Related U.S. Application Data

[63] Continuation-in-part of Ser. No. 81,115, Feb. 24, 1987, Pat. No. 4,846,176.

[51] Int. Cl.$^5$ .............................................. A61F 7/00
[52] U.S. Cl. ..................................... 128/400; 165/46;
128/379
[58] Field of Search ............................... 128/399–403,
128/379; 165/46

[56]  References Cited

U.S. PATENT DOCUMENTS

| | | | |
|---|---|---|---|
| 2,595,328 | 5/1952 | Bowen | 128/403 |
| 3,967,627 | 7/1976 | Brown | 128/400 |
| 4,846,176 | 7/1989 | Golden | 128/400 |

Primary Examiner—William H. Grieb
Assistant Examiner—Mark S. Graham
Attorney, Agent, or Firm—Dykema Gossett

[57] ABSTRACT

A thermal bandage including a conforming member which is adapted to be placed against the skin to uniformly heat or cool the skin area and a thermal pack which is mounted to the conforming member to provide the necessary thermal change to heat or cool the adjacent skin area. In the preferred embodiment, the conforming member includes a thin pliable outer material enclosing a heat conductive substance such as a glycol gel or liquid. The conforming member is in complete contact with the skin to insure uniform heat transfer therebetween. Further, a fluid circulating temperature control device is attached to the thermal bandage for providing the proper heating or cooling as desired. At a preferred embodiment, the thermal pack and conforming member consists of multiple layers of thermoplastic material which are joined to form a first chamber for the heat conductive gel or liquid and a second chamber for the circulation of a thermal fluid between the thermal bandage and the fluid circulating and temperature control device.

7 Claims, 7 Drawing Sheets

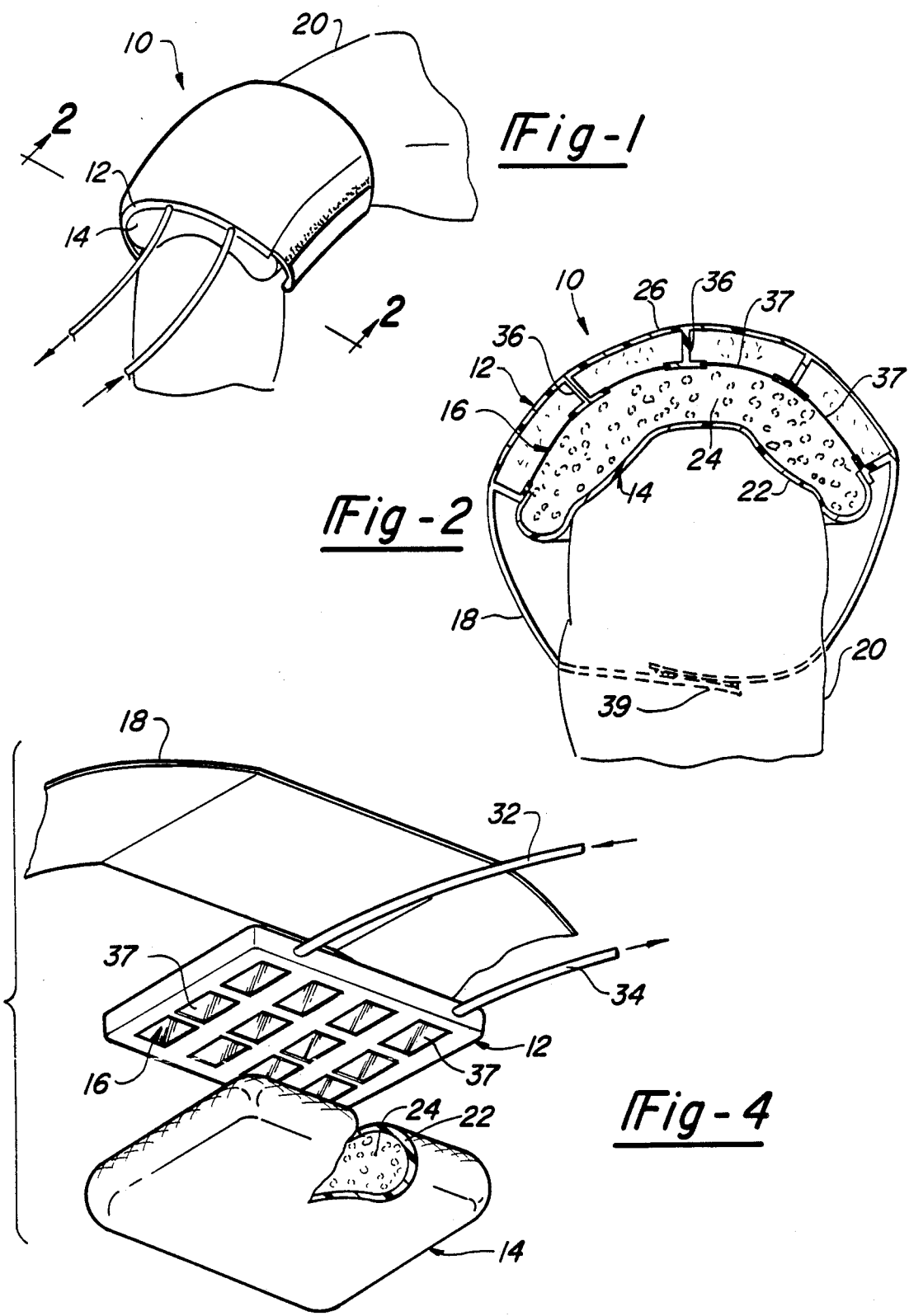

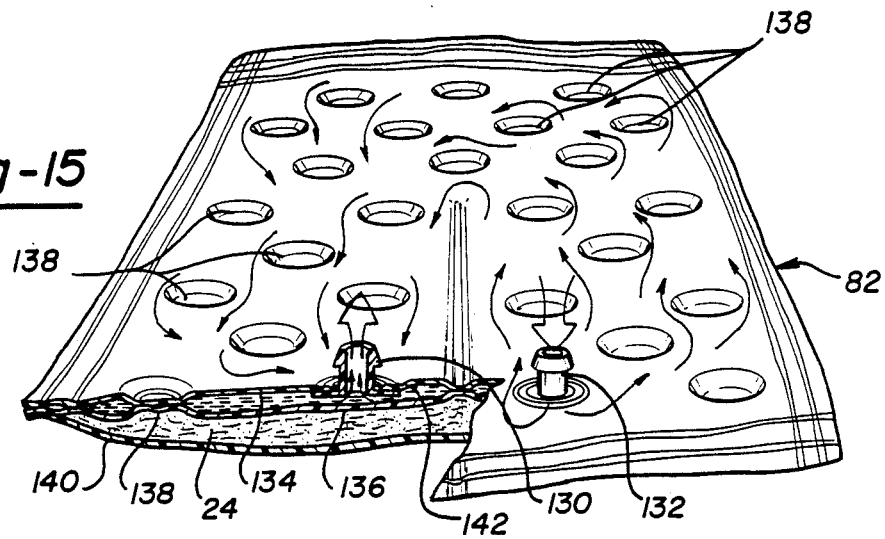
_Fig-15_
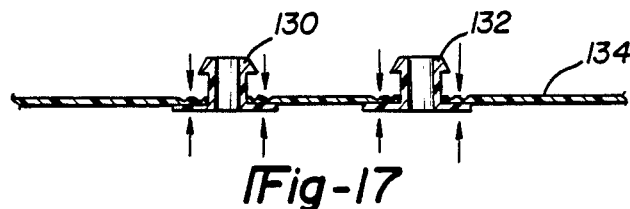
- HEAT SEAL PORTS TO TOP LAYER
- HEAT SEAL SECOND LAYER IN SELECTED LOCATIONS FIG-18
- HEAT SEAL 3rd LAYER ON 3 SIDES FIG-19
- ADD GEL TO PAD
- HEAT SEAL 4th SIDE
_Fig-16_
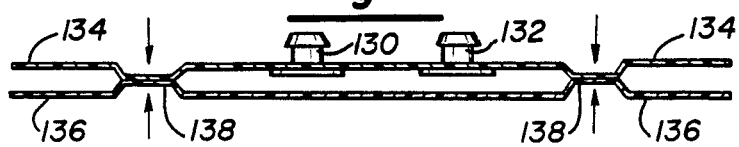
_Fig-17_
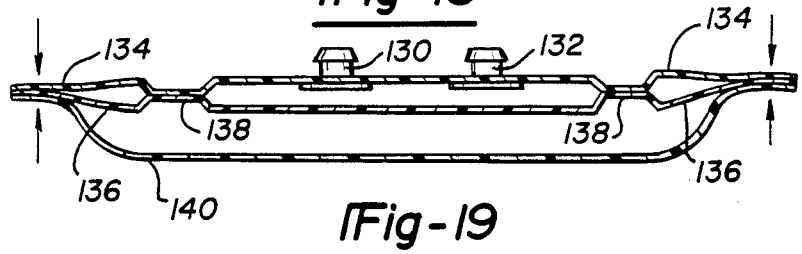
_Fig-18_
_Fig-19_

THERMAL BANDAGE

BACKGROUND OF THE INVENTION

This is a continuation-in-part of my prior application Serial No. 018,115, which was filed on Feb. 24, 1987. Now U.S. Pat. No. 4,846,176, Jul. 11, 1989.

The present invention relates to a thermal bandage for heating or cooling various portions of the human body and more particularly, to a thermal bandage which readily conforms to the contours of a body portion to maintain the adjacent skin at a predetermined uniform temperature to aid in healing and the like. Further, the present invention relates to the fluid circulating system for the thermal bandage and the method of producing the thermal bandage.

A number of thermal applicators exist in the prior art in which thermal fluid is circulated through the applicator to provide a continuous transfer of heat. Examples of this type of applicator are shown in U.S. Pat. Nos. 1,896,953; 2,726,658; and 3,683,902 which are incorporated by reference herein for teaching systems in which such applicator units may be used and for teaching thermal fluid storage and circulation means for said systems. Further, the prior art discloses sealed containers having a heat storing substance for applying heat to a body by transfer of the heat from the container to the body as shown in U.S. Pat. No. 2,595,328. Moreover, there have been prior art attempts to provide a method of controlling tissue hypothermia and for providing a fluid circulating system for use with a thermal blanket or pad, such as disclosed in U.S. Pat. Nos. 3,865,116 and 4,459,468, respectively.

The above applicators and systems suffer from many shortcomings. Typically the applicators involve relatively thick bulky compresses which do not conform closely to the contour of the body. Failure of the compress to conform closely and to retain close contact once positioned, results in irregular heating and cooling of the ski area. This problems often results in irregular or non-uniform healing of the skin, swelling, and the like.

To overcome the above disadvantages, the Applicant of the present invention developed a bendable thermal pack unit disclosed in U.S. Pat. No. 4,108,146 which is included herein by reference. The disclosed invention there provides a thermal pack unit which is configured to the general shape of the body portion to which it is to be applied. That unit overcame the earlier shortcomings by providing a thermal pack unit which conformed to the contour of the human body so that regular and uniform healing of the skin could be obtained. Further, the Applicant of the present invention also developed another uniform cooling pack which is disclosed in U.S. Pat. No. 4,098,279 which is also incorporated by reference herein.

Although Applicant's earlier bendable thermal pack unit possesses superior qualities and greatly improves over the prior art, it requires a different unit for each different body portion. It may be necessary to have numerous sizes of a specific bandage to cover the wide range of human sizes. Consequently, a doctor would have to invest in a huge inventory of different bandages for different anatomic sites and different sizes per site.

The present invention eliminates the deficiencies of the prior art and provides a simple, low cost, light weight thermal bandage which readily conforms to the contours of any portion of the human body to maintain uniform heating or cooling of the adjacent skin area. Further, the thermal bandage of the present invention is easily manufactured using the method disclosed herein. Moreover, a fluid circulating system is disclosed for use with the thermal bandage of the present invention so that both heating and cooling effects may be produced to provide the proper heating or cooling as desired.

BRIEF SUMMARY OF THE INVENTION

The present invention provides a thermal bandage which readily conforms to the contours of a portion of a human body to heat or cool adjacent skin areas. The bandage has a conforming member of supple heat conductive material adapted to readily conform to any contour of the body portion upon application to permit uniform distribution or extraction of heat. Further, the bandage includes a thermal pack mounted to the conformable member with means to either heat or cool the conforming member, and therefore, adjacent skin surface. Finally, the bandage may include a conductive surface separating the conforming member and thermal pack.

In the preferred embodiment, the heat conductive material includes a heat conductive fluid contained within a thin pliable outer material. The outer material is fixed about its perimeter to the thermal pack so that the fluid is in direct contact with it. This provides the most efficient transfer of heat or cooling between the thermal pack and the outer pliable material. In addition to containing the fluid, the thin pliable outer material may also act as a sterile dressing to cover the adjacent skin portion to prevent infection. In a further embodiment, the conforming and pliable outer material is made of a heat conductive thermoplastic material which is capable of readily conforming to the contour of the body portion.

The thermal pack of the preferred embodiment uses thermal fluid to heat or cool the conforming member, which includes the heat conductive fluid that is contained within the thin pliable outer material. The thermal pack is flexible so that it can be bent to the general contours of the body portion. In one embodiment, the pack includes a base, upstanding perimeter walls and a fluid flow chamber defined by the base, walls and conducting surface. The chamber has at least one separator which defines a circuitous flow path through the thermal pack. In this manner, either cooling fluid or heating fluid may be passed through the thermal pack along the flow path to provide uniform heat distribution to the skin area. In a further embodiment, the thermal pack employs thermoelectric means for heating and cooling. In the preferred embodiment, the thermal pack includes two sheets of thermoplastic material which are heat sealed in selected locations to provide for a circuitous flow path for thermal fluid which is pumped through the pack and wherein a third sheet of thermoplastic material is heat sealed to the pack with the heat conductive fluid being contained therebetween.

The conductive surface, which may separate the thermal pack and conforming member, can be constructed of a plurality of separate conducting plates mounted to the thermal pack at the free ends of perimeter walls and separators. All of the plates would be substantially within the same plane with one surface of each plate being exposed to the thermal pack and the opposite surface of each plate being in contact with the thermal conducting fluid or material. The conducting plates separate the thermal pack from the conforming member and permit the transfer of heat between them. In a further embodiment, a single flexible conducting plate may be provided which functions in the same manner as the plurality of plates.

A fluid circulating system for use with the thermal bandage of the present invention is also disclosed for providing the proper heating or cooling as desired. The fluid circulating system is packaged within a small container so that it is readily transportable and usable with the thermal bandage. Precision temperature control is also provided as a result of the fluid circulating system and the configuration of the thermal bandage. Thus, the present invention includes the thermal bandage and the method of making it as well as the fluid circulating system for use with the thermal bandage.

BRIEF DESCRIPTION OF THE DRAWINGS

FIG. 1 is a perspective view of a thermal bandage of the present invention applied to a body portion.

FIG. 2 is a cross-sectional view taken along line 2—2 of FIG. 1.

FIG. 4 is a perspective exploded view of a thermal bandage of the present invention.

FIG. 15 is a perspective view of another form of the thermal bandage partially cut-away for easier viewing.

FIG. 16 is a block diagram illustration of the method for making the thermal bandage illustrated in FIG. 15.

FIG. 17 is a partial cross-sectional view illustrating a step in the manufacturing of the thermal bandage.

FIG. 18 is a partial cross-sectional view illustrating another step in the manufacturing of the thermal bandage.

FIG. 19 is a partial cross-sectional view illustrating yet another step in the manufacturing of the thermal bandage.

DETAILED DESCRIPTION OF THE INVENTION

Figure 3:
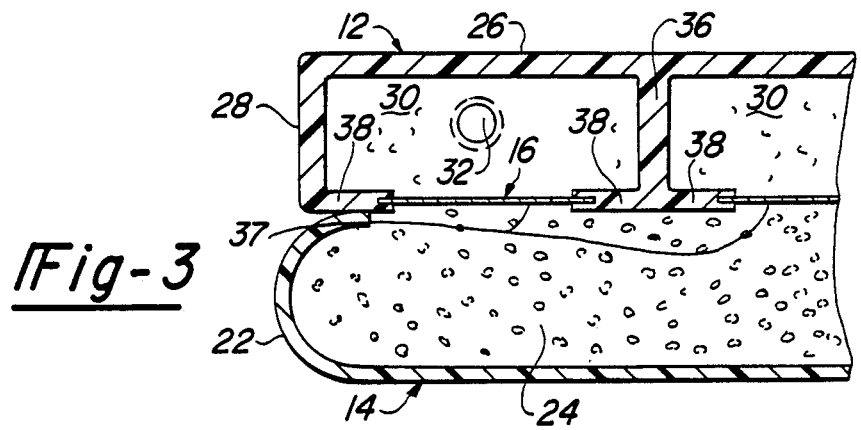
FIG. 3 is a partial cross-sectional view of the thermal bandage of FIG. 2.

With reference to FIG. 1, one form of the thermal bandage of the present invention is indicated generally at 10 and, for purposes of illustration, it is shown attached to a body portion 20 for thermal treatment of the adjacent skin area. To be effective, particularly after surgery, a thermal bandage must uniformly heat or cool a skin area, otherwise complications may arise, such as for example, swelling of the skin area or possible destruction of newly applied skin before the flow of blood to the skin can begin. The thermal bandage of the present invention provides the needed uniform heat transfer because of its ability to readily conform to the contours of a body portion.

Referring now to FIG. 2, thermal bandage 10 includes a conforming member 14 which is placed against the skin. A thermal pack 12 is mounted to member 14 to provide the necessary thermal change to heat or cool the adjacent skin area. A thermal conducting surface 16, such as for example a pliable metal plate, is interposed between the conforming member 14 and the thermal pack 12 to separate them and to facilitate heat transfer between them. As is apparent from FIGS. 1 and 2, conforming member 14 readily conforms to the exact contour of the body portion to ensure a uniform temperature across the skin. Further, thermal pack 12 and conducting surface 16 bend to retain contact between member 14 and the skin. As shown in FIG. 2, a strap 18 is provided to hold bandage 10 in place.

As shown in FIGS. 3-4, the conforming member 14 includes a thin pliable outer material 22, such as for example, a fluid tight cloth or cellophane-type material that encloses a heat conductive substance 24 which can readily adapt to the shape of any object it contacts. Substance 24 may be, as for example, a glycol gel or liquid. The outer saterial 22 is connected along its free ends to the perimeter of thermal pack 12 by adhesive or the like so that the conductive substance 24 is in direct contact with conducting surface 16. In this way, the heat or cooling transferred through surface 16 is directly received by or extracted from substance 24.

In a further embodiment of the present invention, the heat conductive substance 24 comprises a heat conductive thermoplastic material which has the capability of readily conforming to the contours of the body portion. In this embodiment, the pliable outer material 22 is not necessary since the thermoplastic material is not in the fluid state; however, the outer material 22 can still be added and be used as a sterile dressing for the skin surface if desired. To further improve the thermal conductivity of the thermoplastic material, a metallic matrix may be interspersed within the thermoplastic.

Figure 5:
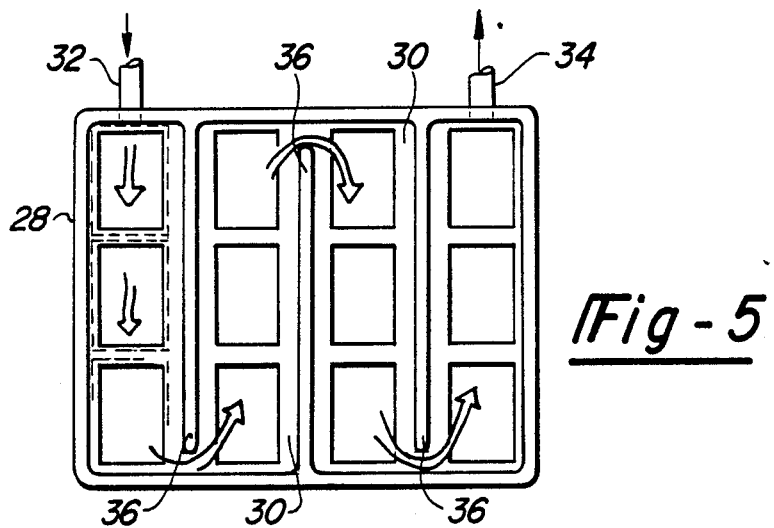
FIG. 5 is a cut-away top view of one embodiment of a thermal pack for the present invention illustrating a fluid flow path.

The thermal pack 12, see FIGS. 2, 3 and 5, may be made of a durable plastic material such as polyvinyl which can be easily bent to the general shape of the body portion. Pack 12 includes a base 26, with perimeter walls 28, and a fluid flow chamber 30 that is defined by walls 28, base 26 and conducting surface 16. Fluid is circulated within chamber 30 between an inlet tube 32 and an outlet tube 34. The circulating fluid is either hot or cold depending upon the application and continually flows over the conducting surface 16 to either transfer heat to or extract heat from the conforming member 14. In this manner, with continuous thermal fluid flow, the adjacent skin area can be maintained at a uniform temperature. Various means are available for circulating and heating or cooling the fluid, as for example, a pump with a temperature control device, as will hereinafter be disclosed.

Referring to FIG. 5, to provide for flow of thermal fluid across the entire surface of conducting medium 16, separators 36 are provided within chamber 30 to give the fluid flow a circuitous or serpentine path. Thus, due to separators 36 the fluid entering at inlet 32 must follow a predetermined path along conducting surface 16 so that the entire surface of conducting surface 16 is traversed by thermal fluid. As can be seen in FIG. 5, separators 36 form channels within chamber 30, alternatively extending from opposed parameter walls 28 leaving only a small opening between the free end of each separator 36 in the opposed wall 28 for the passage of fluid.

Figure 6:
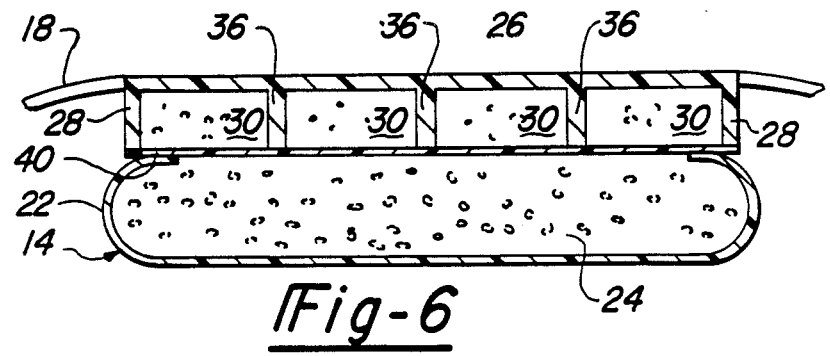
FIG. 6 is a cross-sectional side view of an alternative embodiment.

The conducting surface 16 is formed by a plurality of substantially equal size metal squares 37 with each square being mounted within flanges 38 on the free ends of the perimeter walls 28 and separators 36. The mounting of the squares to flanges 38 completes the channel and prevents thermal fluid leakage. With reference to FIG. 6, a further embodiment of surface 16 is illustrated having a single flexible sheet 40 which is secured to the free ends of perimeter walls 28 and separators 36 by, as for example, an adhesive. Flexible sheet 40 may be made of a flexible metal such as aluminum.

In use, the thermal bandage 10 is placed against the body portion with the conforming member 14 in contact with the skin area. Strap 18 is wrapped around the body portion and fastened, as for example, by a Velcro-type fastener 39 (Velcro is a synthetic material which adheres when pressed together). The flexible thermal pack 12 and conducting surface 16 bend to the general shape of the body portion to assist in keeping the conforming member 14 in contact with the skin area. After bandage 10 is attached, a thermal fluid source is connected between inlet 32 and outlet 34 for circulating hot or cold fluid through thermal pack 12. In this manner, heat is either added to or extracted from the skin area.

Figure 7:
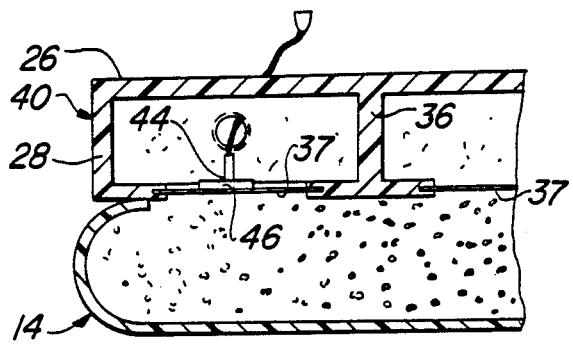
FIG. 7 is a partial cross-sectional side view of an alternative embodiment.
Figure 8:
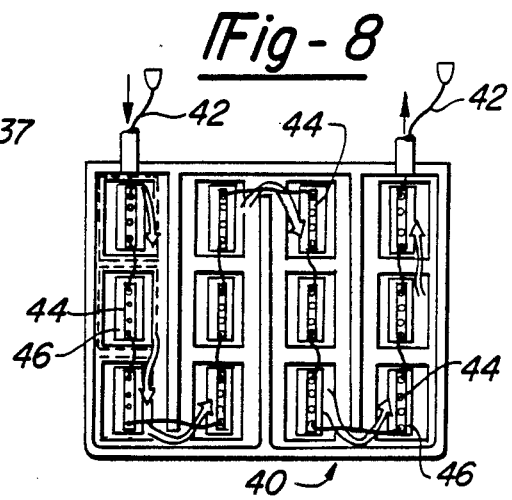
FIG. 8 is a cut-away top view of the device of FIG. 7.

Referring now to FIGS. 7 and 8, a further embodiment of the present invention is shown employing a thermoelectric pack 40. Preferably, pack 40 has a flexible base 26 with perimeter walls 28 and separators 36 for mounting conducting squares 37. A series of electrically interconnected electrodes 44 are mounted to squares 37. Insulators 46 are interposed between squares 37 and electrodes 44. An electrical lead 42 connects electrodes 44 with a power source (not shown). Upon energizing the power source, an electric current flows through each electrode 44 producing thermoelectric heat or cold flow which in turn raises or lowers the temperature of the conforming member 14. It is within the intended scope of this invention to use other thermoelectric devices to provide the necessary heating and cooling of the conforming member, such as, for example, a peltier device may be used which permits both heating and cooling by the use of dissimilar materials and electric current, and an example of such a device is disclosed herein below.

Figure 9:
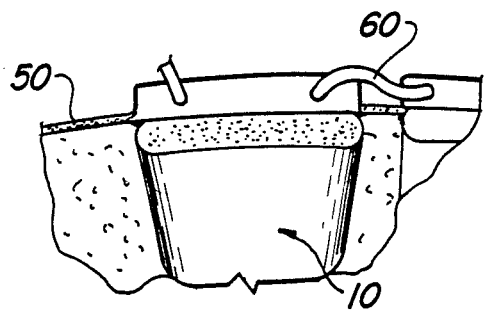
FIG. 9 is a partial perspective view of a further embodiment.
Figure 10:
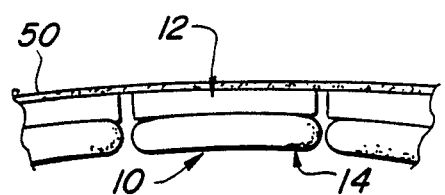
FIG. 10 is a side view of the device illustrated in FIG. 9.

Because of the ability of conforming member 14 to readily adapt to any contour immediately upon contact, a standard bandage 10 as described above can be used for almost all applications. For example, a surgeon can use the standard thermal bandage 10 of the present invention to heat or cool a knee, joint, or body surface. Further, as illustrated in FIGS. 9 and 10, the versatility of the thermal bandage of the present invention allows the bandage to be manufactured and distributed on a sheet 50 from which bandages 10 may be removed. Preferably, sheet 50 is cut to remove a single bandage 10 or multiple bandages 10 if a larger skin area must be covered. Connectors 60 interconnect the individual bandages and when cut in the location between adjacent bandages, they form an inlet 32 and outlet 34 for fluid or the electrical leads 42, as described previously.

Figure 11:
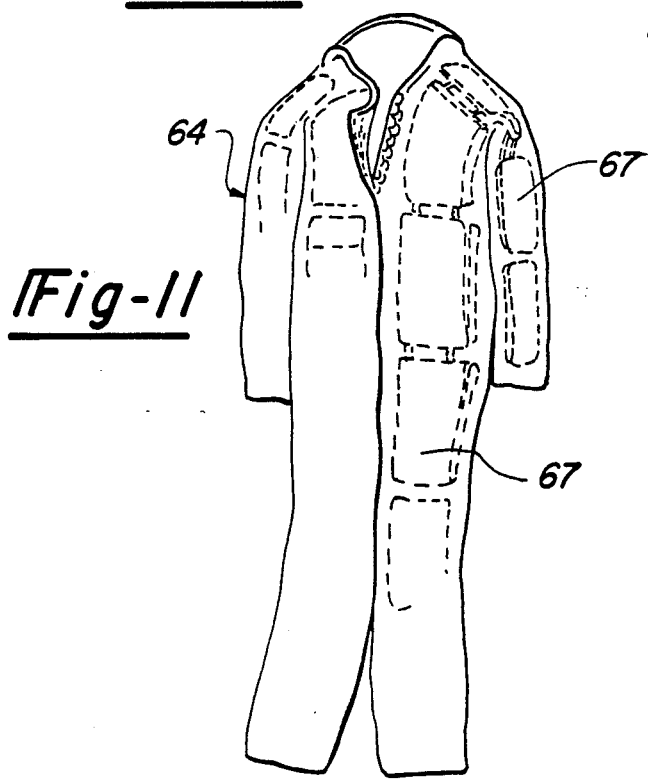
FIG. 11 is a perspective view of a garment employing the device of the present invention.

Referring now to FIG. 11, a thermal garment 64 is illustrated employing a plurality of thermal bandages 10. The garment 64 has a plurality of pockets or areas 67, shown in phantom, into which the thermal bandages can be placed. Garment 64 permits extremely large areas of the body to be thermally treated in a uniform manner. Preferably, the bandages 10 have thermoelectric packs which can be connected in series so that one electrical source can be used. This electrical source can be carried by the individual who can then move as desired. Further, a thermal pack using fluid can also be used.

Referring now to FIGS. 12-22, a fluid circulating and temperature control device 80 is disclosed in combination with another form of the thermal bandage which is indicated generally at 82. The fluid circulating and temperature control device 80 is designed such that it may be used in connection with any of the thermal bandages made in accordance with the present invention for providing the proper heating or cooling as desired. It is housed in a compact and easily transportable case 84 so that it is available for use at all times.

Figure 14:
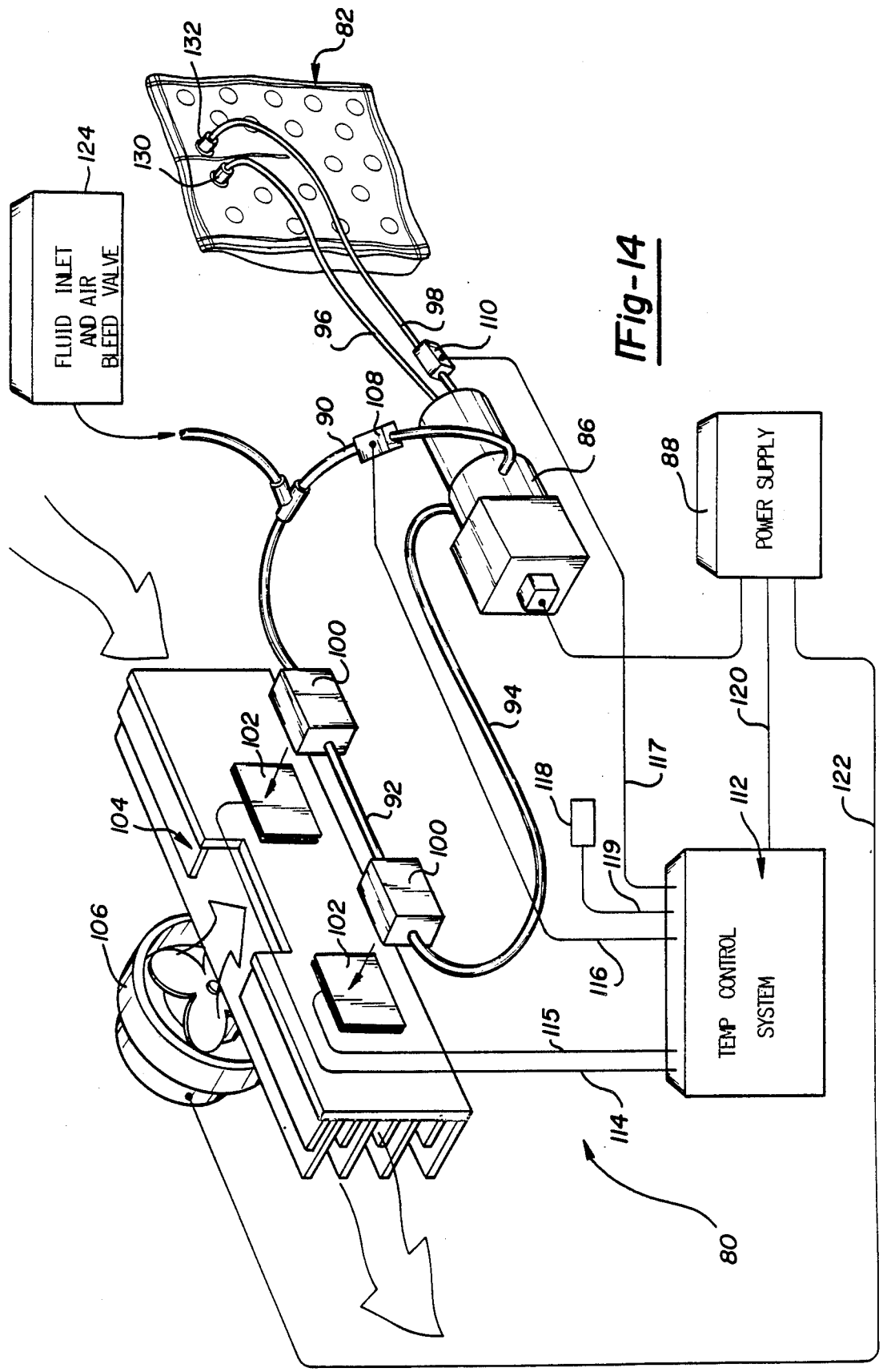
FIG. 14 is a schematic assembly view of the fluid circulating device.

In order to circulate fluid through the thermal bandage 82, a pump 86 is connected to a power supply 88 as shown in FIG. 14. Fluid is directed through lines 90, 92, 94, as will be described. Further, fluid is directed to thermal bandage 82 through line 98, and fluid is returned from thermal bandage 82 to pump 86 through line 96. The fluid circulating and temperature control device 80 further includes a heat exchange assembly comprising thermal modules 100, peltier devices 102, heat dissipating structure 104, and fan 106. Further, heater 108 and temperature sensor 110 are provided in lines 90 and 98 respectively for the purpose of heating the fluid when necessary and monitoring the temperature of the fluid being directed to thermal bandage 82.

Figure 12:
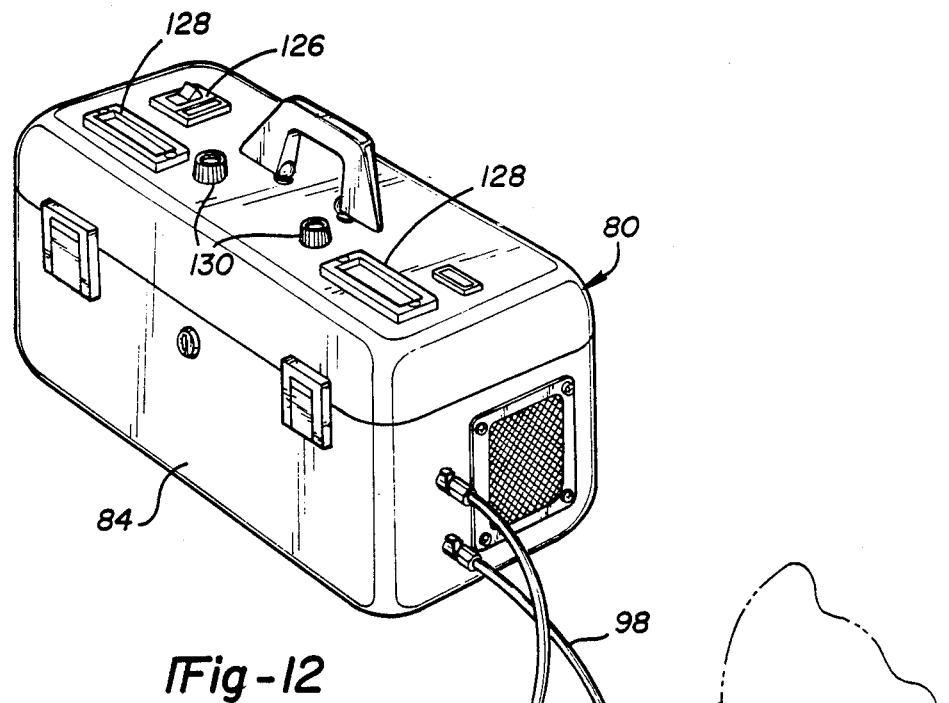
FIG. 12 is a perspective view of the compact and portable fluid circulating device in combination with the thermal bandage.
Figure 13:
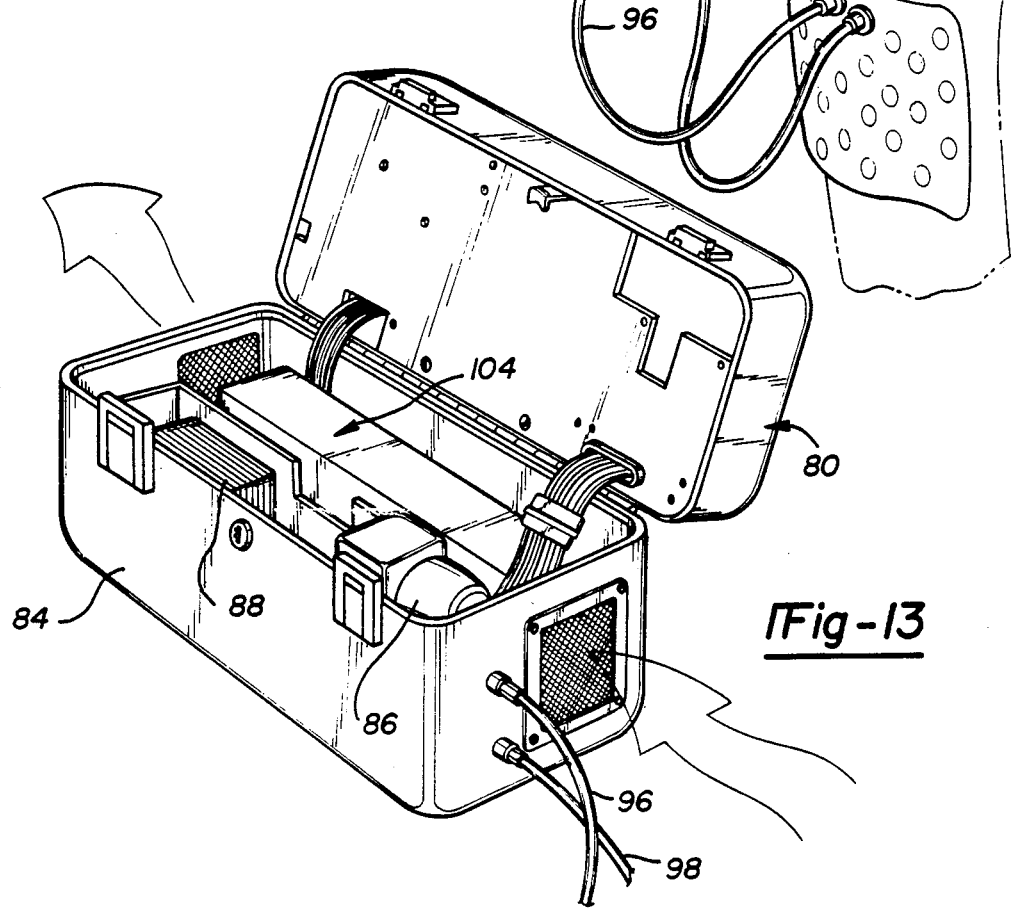
FIG. 13 is a perspective view of the fluid circulating device.

A conventional temperature control system and circuit 112 is electrically interconnected by leads 114 and 115 to the peltier devices 102, and by leads 116 and 117 to the heater 108 and temperature sensor 110. Further, the temperature of the skin area may be determined by a conventional temperature sensor means 118 which is also interconnected to temperature control system 112 by lead 119. As illustrated in FIG. 14, temperature control system 112 is connected to power supply 88 by lead 120 and fan 106 is connected to power supply 88 by lead 122. Further, a conventional fluid inlet and air bleed valve 124 is connected to fluid conduit 90 so that fluid may be added as necessary and for the purpose of preventing cavitation in pump 86. Finally, as shown in FIG. 12, a switch 126 is provided for turning the power supply 88 "on" and "off"; digital displays 128 are provided for permitting a readout of the desired and actual fluid temperatures from pump 86; and manual control knobs 130 are provided for adjusting the desired fluid temperature and for brightness control of the digital display.

Referring now to FIGS. 15-21, the preferred thermal bandage and method of making same is illustrated. As shown in FIGS. 16 and 17, ports 130 and 132 are united to a sheet 134 of water impervious material by heat sealing. Next, a second sheet of water impervious material 136 is heat sealed to the first sheet 134 in selected locations 138, as illustrated in FIGS. 15 and 18. A third layer of material 140 is heat sealed at its perimeter to join with the perimeters of material layers 134 and 136. Three edges or sides of the layers 134, 136 and 140 are joined together so that a glycol gel or liquid may be thereafter interposed between layers 136 and 140, as shown in FIGS. 16 and 19. Finally, the remaining edge of layers 134, 136, and 140 are heat sealed together to complete the assembly of the thermal bandage 82.

Thus, a fluid 142, such as water, may be circulated between ports 130 and 132 within the chamber formed between layers 134 and 136. The circulating fluid may either be hot or cold depending upon the application required. Further, the circulation fluid 142 continually flows over the conducting surface 136 in a circuitous flow path as shown in FIG. 15 to either transfer heat to or extract heat from the glycol gel or liquid 24 and conforming layer 140. In this manner, with continuous thermal fluid flow, the adjacent skin area can be maintained at a uniform temperature.

Figure 20:
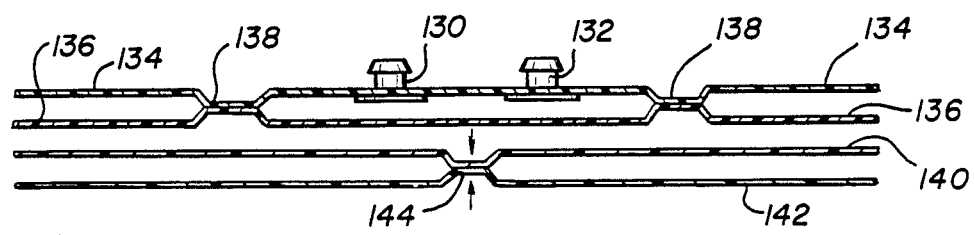
FIG. 20 is a partial cross-sectional view illustrating an alternative method step in preparing the thermal bandage.
Figure 21:
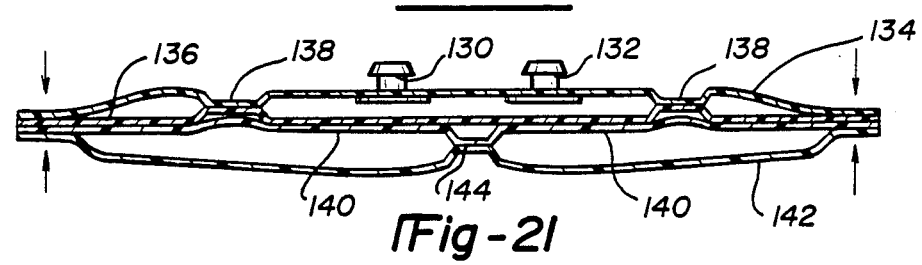
FIG. 21 is a partial cross-sectional view illustrating a completed thermal bandage assembly utilizing the method steps shown in FIG. 20.

FIGS. 20 and 21 illustrate yet another form of the thermal bandage 82. The steps which were described previously for joining ports 130 and 132 to layer 134 and thereafter heat sealing layer 136 to layer 134 in selected locations 138 are the same for this form of the thermal bandage 82. However, in the method shown in FIGS. 20 and 21, a fourth layer 142 is joined to the third layer 140 at selected locations 144 by heat sealing. Thereafter, all of the layers are joined together on three of their perimeter sides and the glycol gel or liquid 24 is added to the chamber formed between layers 140 and 142. The assembly is then completed by heat sealing the remaining perimeter edges of the layers together to form a completed thermal bandage 82.

Figure 22:
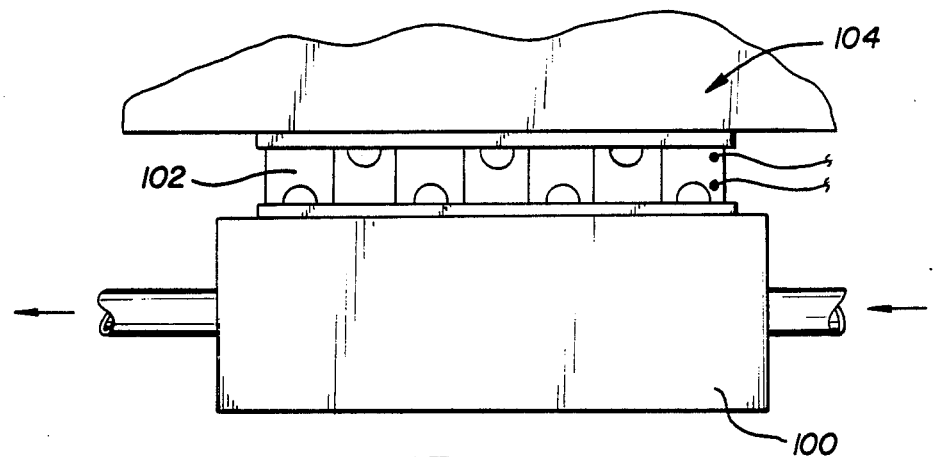
FIG. 22 is a partial top plan view of the manifold and thermal electric device for the heat exchanger.

Referring now to FIG. 22, the interface between thermal module 100, peltier device 102, and heat dissipating structure 104 is illustrated. The thermal modules 100 are structured to provide a temporary reservoir for the circulating fluid such that an adequate amount of residence time is permitted for effecting the proper heating or cooling of the fluid. In operation, the temperature is sensed within the fluid through operation of the temperature sensor 110. The fluid is circulated through the thermal modules 100 to carry away or add heat by means of the peltier devices 102. Further, the fan 106 circulates air across the vanes of the heat dissipating structure 104 to assure the desired cooling of the components in the system. Thus, the precision in temperature control for the thermal bandage 82 results from the configuration of the bandage as well as the temperature control afforded by the fluid circulating and temperature control device 80.

With this detailed description of the thermal bandage of the present invention and the operation thereof, it will be obvious to those skilled in the art that various modifications can be made to the thermal bandage and in the materials and specific configurations used therein without departing from the spirit and scope of the present invention which is defined by the appended claims.

What is claimed is:

1. A thermal bandage adapted to closely conform to the contours of a portion of a human body to heat or cool the adjacent skin area; said thermal bandage comprising:

a conforming member forming one side of said thermal bandage and including supple heat conducting material which readily conforms to the contour of said body portion such that said conforming member is in complete contact with said skin area permitting uniform distribution or extraction of heat from said skin area, and said conforming member including an outer thin pliable material surface which encloses said heat conducting material, and said outer pliable material surface having end portions;

a thermal pack mounted to said conforming member and forming an opposite side of said thermal bandage, said thermal pack being coextensive with the conforming member and said pack having means to heat or cool said conforming member;

a single boundary layer heat conducting surface interposed between said conforming member and said pack to separate said thermal pack and said conforming member and to facilitate the conduction of heat thereacross;

said heat conducting material includes a first heat conductive fluid contained between said thin pliable outer material surface and said single boundary layer heat conducting surface, said pliable outer material being fixed at its end portions to said thermal pack such that said first heat conductive fluid is in contact with said heat conducting single boundary layer surface and only said conforming member contacts said skin area;

said heating or cooling means providing for the circulation of a second heat conductive fluid under pressure through said thermal pack and over said single boundary layer conducting surface to either transfer heat to or extract heat from said first heat conducting fluid, said heating or cooling means including means for monitoring the temperature of the second heat conductive fluid for thermostatically controlling the temperature of the boundary layer surface, first heat conductive fluid, and said outer material surface so as to maintain a desired temperature at the skin area.

2. The thermal bandage as defined in claim 1, wherein said heating or cooling means comprises a pump which directs said second heat conductive fluid to and from said thermal bandage through at least a first fluid conduit.

3. The thermal bandage as defined in claim 2, wherein a second fluid conduit is connected to said pump for circulating said second heat conductive fluid through at least one module means, a thermoelectric means, said module means being in close proximity to said thermoelectric means, and said module means providing sufficient residence time for said second heat conductive fluid at said thermoelectric means to permit a desired heat exchange to occur between said second heat conductive fluid and said thermoelectric means.

4. The thermal bandage as defined in claim 3, wherein said first conduit includes a temperature sensing means and said second conduit includes heating means.

5. The thermal bandage as defined in claim 4, wherein said thermoelectric means is positioned between said module means and a heat dissipating means.

6. The thermal bandage as defined in claim 1, wherein said outer material surface, said single boundary layer, and said thermal pack includes multiple layers of thermoplastic material which are joined together at said end portions.

7. The thermal bandage as defined in claim 6, wherein two of said layers are attached together at various selected locations to form said pack and said single boundary layer, and another of the layers is attached to said two layers to form said outer material surface which encloses said first heat conductive fluid, wherein second heat conductive fluid is circulated under pressure between said two layers.

* * * * *